United States Patent

Clark, Jr. et al.

[11] Patent Number: 5,299,458
[45] Date of Patent: Apr. 5, 1994

[54] NONDESTRUCTIVE ULTRASONIC EVALUATION OF FORMABILITY OF METALLIC SHEETS

[76] Inventors: Alfred V. Clark, Jr., 2590 Vassar Dr., Boulder, Colo. 80303; R. Bruce Thompson, 3212 Kingman Ave., Ames, Iowa 50010

[21] Appl. No.: 989,914

[22] Filed: Dec. 11, 1992

Related U.S. Application Data

[63] Continuation of Ser. No. 485,038, Feb. 26, 1990, abandoned.

[51] Int. Cl.$^5$ ............................................. G01N 29/18
[52] U.S. Cl. .......................................... 73/597; 73/643
[58] Field of Search ................. 73/597, 598, 602, 643, 73/644, 645

[56] References Cited

U.S. PATENT DOCUMENTS

| | | |
|---|---|---|
| 4,334,431 | 6/1982 | Kohno et al. . |
| 4,375,167 | 3/1983 | Nusbickel, Jr. et al. ............. 73/644 |
| 4,432,234 | 2/1984 | Jones ..................................... 73/597 |
| 4,466,287 | 8/1984 | Repplinger et al. . |
| 4,522,071 | 6/1985 | Thompson ............................ 73/643 |
| 4,574,634 | 3/1986 | Pappano ................................ 73/597 |
| 4,594,897 | 6/1986 | Bantz . |
| 4,789,431 | 12/1988 | Typpo . |
| 4,790,188 | 12/1988 | Bassiere et al. ....................... 73/597 |
| 4,800,757 | 1/1989 | Hashinoki et al. . |
| 4,899,589 | 2/1990 | Thompson et al. ................... 73/597 |
| 4,926,692 | 5/1990 | Brokowski et al. .................. 73/597 |

OTHER PUBLICATIONS

Ultasonic Measurement of Formability in Thin Ferritic Steel Sheets, by A. V. Clark et al., Jul 31–Aug. 5 1988 Review of Progress in Quantative NDE Photograph of Modul-r measurement instrument. (No date, but admitted to be prior art).

Ultrasonic Measurement of Sheet Anisotrophy and Formability, by A. V. Clark et al., SAE International Cong. & Exposition, Feb. 27–Mar. 3, 1989.

Primary Examiner—Hezron E. Williams
Assistant Examiner—Rose M. Finley
Attorney, Agent, or Firm—Gregory Garmong

[57] ABSTRACT

An indication of the formability of metallic sheet is determined using a correlation between nondestructively measurable ultrasonic properties and a formability index. A calibration relation is initially established by measuring ultrasonic velocities at various angles to the rolling direction of sheet specimens with noncontacting electromagnetic acoustic transducers, calculating an ultrasonic correlation parameter from the measurements, destroying the specimens in tensile tests to measure a formability index, and then correlating the ultrasonic correlation parameter with the formability index. Once this relationship is established, the formability index of a working sample, which is not to be destroyed, is found by making the same types of ultrasonic property measurements on the working sample, calculating the ultrasonic correlation parameter for the working sample, and then employing the previously established correlation to ascertain the formability index for the working sample.

1 Claim, 4 Drawing Sheets

NONDESTRUCTIVE ULTRASONIC EVALUATION OF FORMABILITY OF METALLIC SHEETS

This application is a continuation of application Ser. No. 07/485,038, filed Feb. 26, 1990, now abandoned.

BACKGROUND OF THE INVENTION

This invention relates to the nondestructive evaluation of the formability of metallic sheet materials such as steel, and, more particularly, to an ultrasonic technique for making such evaluations.

One of the largest tonnage uses of steel throughout the world is found in the preparing of thin flat sheets by rolling, and then forming the sheets into useful products. Most of the exterior of an automobile is made of formed steel sheets, for example. Steel sheet material is also used in siding, appliances, office equipment, containers, and a myriad of other products.

One common forming procedure is die forming, wherein the steel sheet is placed between a male die and a female die in a press. As the press closes, the sheet of steel is deformed into the shape dictated by the closed dies. Other sheet forming techniques such as bending, drawing, and ironing are also used for particular products.

Most of the steel used in sheet forming is a low carbon steel of 0.05-0.20 weight percent carbon in iron, with minor amounts of other elements present. Studies over the years have shown that such steels, as well as many other sheet materials, do not deform uniformly in sheet forming operations, due to textures created as the sheet is rolled from thicker stock. The textures result from crystallographic preferred orientations in the rolled sheet.

The nonuniform deformation of the steel sheet leads to various types of problems with the formed sheet products. In the extreme case, the steel may fail in the forming operation, such as by tearing, so that a part cannot successfully be formed. In less severe situations, there may be nonuniform thinning of the formed sheet product so that there are local thin regions or there may be nonuniform strains around the edges of the sheet known as "ears", for example.

The occurrence of these problems depends upon many factors, including the nature of the forming operation, the type of metal, melting practice for the metal, composition variations in the metal, the heat treatment of the metal, and the sequence of rolling steps used to prepare the flat sheet. While it would be desirable to determine the optimum set of conditions for these parameters and then hold them constant, such precise control is simply not possible for the very large quantities of metal used and the present state of manufacturing technology.

Consequently, various types of tests have been developed to evaluate the formability of sheet material before an attempt is made to form it. These tests generally utilize destructive measurements of mechanical properties of sheet material to determine a formability index. If the formability index is within certain allowed values, then the sheet material is judged to be acceptable for the particular forming operation and is shipped to the user for forming. On the other hand, if the formability index does not meet the required limitations, the sheet must be diverted for other, less demanding uses, or scrapped.

While the basic viability and utility of the formability index approach as a cost-saving procedure has been established, it suffers from some important shortcomings in a typical industrial setting. Presently operable techniques for measuring the formability index require that the sample being evaluated be either destroyed by mechanical testing, or at the least excised from the larger sheet in which it is embedded. This requirement is not fatal to the use of the test, but it does mean that there is a delay in obtaining test results, that it is impossible to perform "on line" measurements on the sheet as it is being rolled, and that at the least there is wasted material when samples are cut from the sheet.

There has been proposed the possibility of measuring a formability index by propagating ultrasonic waves of different types (i.e., shear waves of differing polarizations) in the plane of the sheet, but no technique has been demonstrated. It has also been proposed to propagate waves through the thickness of a sheet to determine a modulus value which is said to be related to a formability index, but again no operable method has been demonstrated.

It would be particularly desirable to have the capability to perform on line tests as the sheet is being rolled, to permit problems to be discovered without delay. Conceivably, the results of such a test could be used to actively control the rolling operation to reduce the incidence of problems caused by rolling speed, roll bites, and other controllable factors.

One possible approach to development of a nondestructive formability evaluation that could be used on line has been the discovery of crystallographically based orientation distribution coefficients, or ODCs. The ODCs can be correlated to the irregular crystallographies that cause formability problems, and can be measured nondestructively and on line with X-ray machines. The ODC approach has the shortcomings that it is heavily based in theory and therefore can be subject to the effects of erroneous assumptions of the theory, and does not take into account many of the variables known to affect sheet formability, such as composition of the sheet material. Moreover, a reflection-mode X-ray measurement samples only textures near the surface, which may not accurately reflect the character of the interior of the sheet. To sample the interior of the sheet, a transmission-mode X-ray measurement must be made, which requires a high-power X-ray source and special detectors, and can be hazardous if there is leakage of the X-rays. Although the ODC approach has some promise, as a result of these problems it has not achieved a wide degree of acceptance in the industrial community.

There remains a need for an improved approach to measuring the formability of sheet materials, preferably by a nondestructive technique that would permit on line measurement and control. The present invention fulfills this need, and further provides related advantages.

SUMMARY OF THE INVENTION

The present invention provides a nondestructive technique for evaluating the formability of sheet materials such as steel. It may be used on line, if desired. The apparatus is relatively compact and light, and can be used in stationary or portable systems. The approach takes account of many possible system variables through the use of a calibration technique. Thus, although the approach is well founded in theory, its operability in any particular situation is not dependent upon satisfaction of theoretical assumptions that could prove to be incorrect. Significantly, the present approach can serve as the basis for communication of sheet formability information between users and manufacturers, as the basis for specifications, and as an approach for on line testing to be certain that sheet material meets the specifications even as it is being rolled.

In accordance with the invention, a process for nondestructively evaluating the formability of rolled metallic sheet comprises the steps of measuring the ultrasonic velocities of sound in the plane of the sheet parallel to a rolling direction $V_o$, perpendicular to the rolling direction $V_{90}$, and at 45 degrees to the rolling direction $V_{45}$, each of said measurements being conducted without excising a sample from the sheet; calculating an ultrasonic correlation parameter dependent upon the measured ultrasonic velocities; and determining a formability index of the sheet from the calculated correlation parameter and a previously prepared calibration between the correlation parameter and the formability index.

More generally, a process for nondestructively evaluating the formability of rolled metallic sheet of a type for which a correlation between an ultrasonic correlation parameter and a formability index has been previously prepared comprises the steps of measuring the ultrasonic velocities of sound in the plane of the sheet along at least three noncolinear directions, each of said measurements being conducted without excising a sample from the sheet; calculating an ultrasonic correlation parameter dependent upon the measured ultrasonic velocities; and determining a formability index of the sheet from the calculated correlation parameter and a previously prepared calibration between the correlation parameter and the formability index.

The preferred approach of the invention utilizes measurements made parallel to the rolling direction, perpendicular to the rolling direction, and at 45 degrees to the rolling direction, all measurements being in the plane of the sheet. Conventional practice for destructively obtaining the formability index utilizes tensile tests made from specimens cut at these angles to the rolling direction, and those in the art conventionally think in these geometrical relations. However, as indicated, any three noncolinear directions in the plane of the sheet can be used, because of the relationship for ultrasonic velocity $v_A$ at angle A in relation to a mean averaged velocity $v_o$, $$v_A = v_o + a \cos 2A + b \cos 4A.$$

The invention also extends to the apparatus for performing such evaluations. In accordance with this aspect of the invention, apparatus for evaluating the formability of a sheet of metal comprises means for measuring the ultrasonic velocities of sound in the plane of the sheet parallel to a rolling direction $V_0$, perpendicular to the rolling direction $V_{90}$, and at 45 degrees to the rolling direction $V_{45}$, each of said measurements being conducted without excising a sample from the sheet; means for calculating an ultrasonic correlation parameter dependent upon the measured ultrasonic velocities; and means for determining a formability index of the sheet from the calculated correlation parameter and a previously prepared calibration between the correlation parameter and the formability index.

The present invention is preferably implemented with noncontacting electromagnetic acoustic transducers (EMATs). A sending EMAT excites and propagates an ultrasonic wave in a sample, and a receiving EMAT spaced a distance from the sending EMAT detects and receives that wave. Through careful calibration of the EMAT apparatus or the use of a three-probe technique, the velocity of the wave through the specimen can be determined, without either EMAT requiring the use of a coupling agent to achieve coupling to the sheet and without the need to excise a sample from the sheet. The paired EMAT apparatus is used to measure velocities of ultrasonic waves parallel to any direction lying in the plane of the sheet. It is readily packaged for laboratory and industrial use.

The velocities in three non-colinear directions in the plane of the sheet are determined. Preferably, those directions are parallel to the rolling direction, perpendicular to the rolling direction, and at an angle of 45 degrees to the rolling direction. The velocities are mathematically combined to form an ultrasonic correlation parameter, which can then be used to determine a formability index using a previously prepared calibration relation between the two. The work underlying the present invention has demonstrated the existence of such a calibration relationship, and the operability of the approach.

The present invention thus provides an approach for evaluating the formability of metal sheet in a nondestructive, noncontacting manner, after a basic calibration relationship has been prepared. Other features and advantages of the invention will be apparent from the following more detailed description of the preferred embodiment, taken in conjunction with the accompanying drawings, which illustrate, by way of example, the principles of the invention.

DETAILED DESCRIPTION OF THE PREFERRED EMBODIMENTS

In accordance with a preferred embodiment of the invention, a process for nondestructively evaluating the formability of rolled metallic sheet comprises the steps of measuring the ultrasonic velocities of sound in the plane of the sheet parallel to a rolling direction $V_o$, perpendicular to the rolling direction $V_{90}$, and at 45 degrees to the rolling direction $V_{45}$, each of said measurements being conducted without excising a sample from the sheet, and including the substeps of sending an ultrasonic wave through the sheet with a sending electromagnetic acoustic transducer, receiving the ultrasonic wave with a receiving electromagnetic acoustic transducer, the sending and receiving transducers having a fixed distance therebetween, measuring the time for a selected zero crossing of the ultrasonic wave to propagate from the sending transducer to the receiving transducer, and determining the ultrasonic velocity using an effective path length distance previously determined for the array of sending and receiving transducers; calculating an ultrasonic correlation parameter dependent upon the measured ultrasonic velocities; and determining a formability index of the sheet from the calculated correlation parameter and a previously prepared calibration between the correlation parameter and the formability index.

Figure 1:
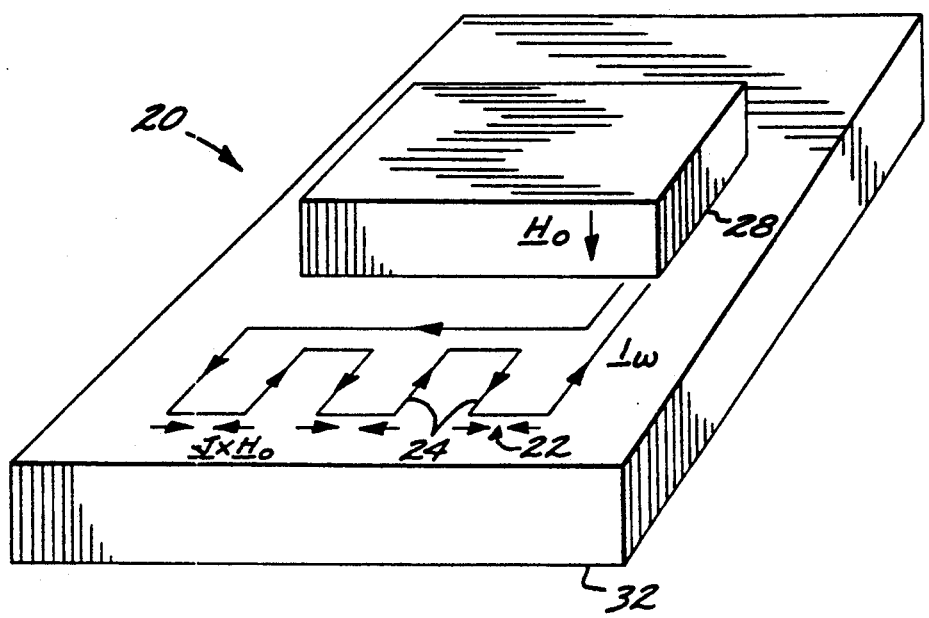
FIG. 1 is a schematic perspective view of an EMAT.
Figure 2:
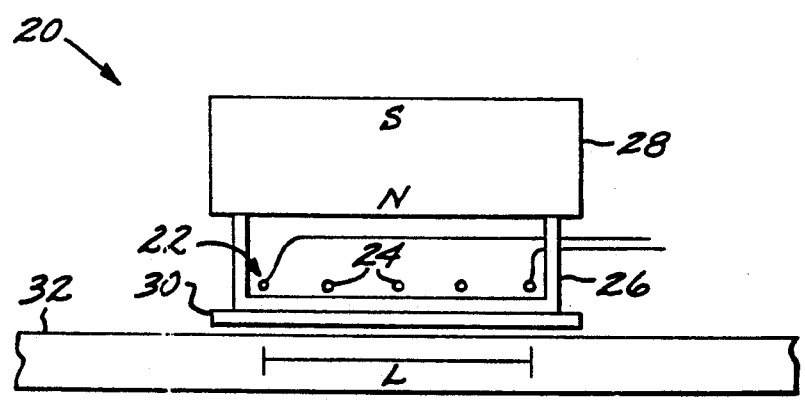
FIG. 2 is a side sectional view of an EMAT.

The preferred embodiment utilizes electromagnetic acoustic transducers (EMATs herein) to generate and to receive an acoustic wave. FIG. 1 schematically illustrates an EMAT 20, and FIG. 2 shows a side sectional view of the EMAT 20. The EMAT 20 includes a meanderline coil 22 of electrically conducting wire, which is a length of wire bent into a series of parallel, coplanar segments 24. The coil 22 is placed within a housing 26, made of a material such as plastic or ceramic, or a thin metal sheet. A magnet 28 is positioned above the meanderline coil 22. On the bottom of the housing 26 is preferably attached a wear plate 30 made of a material such as plastic that is preferentially worn away in the event that the EMAT 20 inadvertently contacts a sheet 32 above which the EMAT 20 is positioned.

The EMAT 20 operates according to the following principle. When a wire 24 positioned above a sheet 32 carries a dynamic current, eddy currents are induced in a near-surface layer of the sheet 32. When a static magnetic bias is applied to the sheet 32 by a magnet 28, the eddy currents experience Lorentz forces which are transmitted to the solid and act as a source of ultrasonic waves. For a ferromagnetic sheet material such as steel, there are ferromagnetic interactions well known in the art. When a number of wires 24 are arranged in a periodic set of elements to form the meanderline coil 22, an antenna is created that excites spatially periodic force in the sheet 32. No contact or couplant between the EMAT 20 and the sheet 32 is required. The operation of the EMAT has been described for a sending or transmitting mode, but the EMAT can also be used in a receiving mode by the operation of reciprocal processes to those just described.

An important feature of any practical EMAT 22 is that it has a finite length L, and that the periodic force that creates the ultrasonic wave is produced over some portion of that length and not at a single point. This mode of operation permits the ultrasonic excitation of symmetrical Lamb waves in the sheet 32, but complicates the determination of velocity to the degree of accuracy required. As will be described subsequently, a technique has been developed for determining the precise effective distance between two EMATs, to permit a computation of the acoustic velocity in the sheet 32.

EMATs have been previously known in the art, see for example U.S. Pat. Nos. 4,466,287 and 4,777,824, whose disclosures are incorporated by reference.

Figure 3:
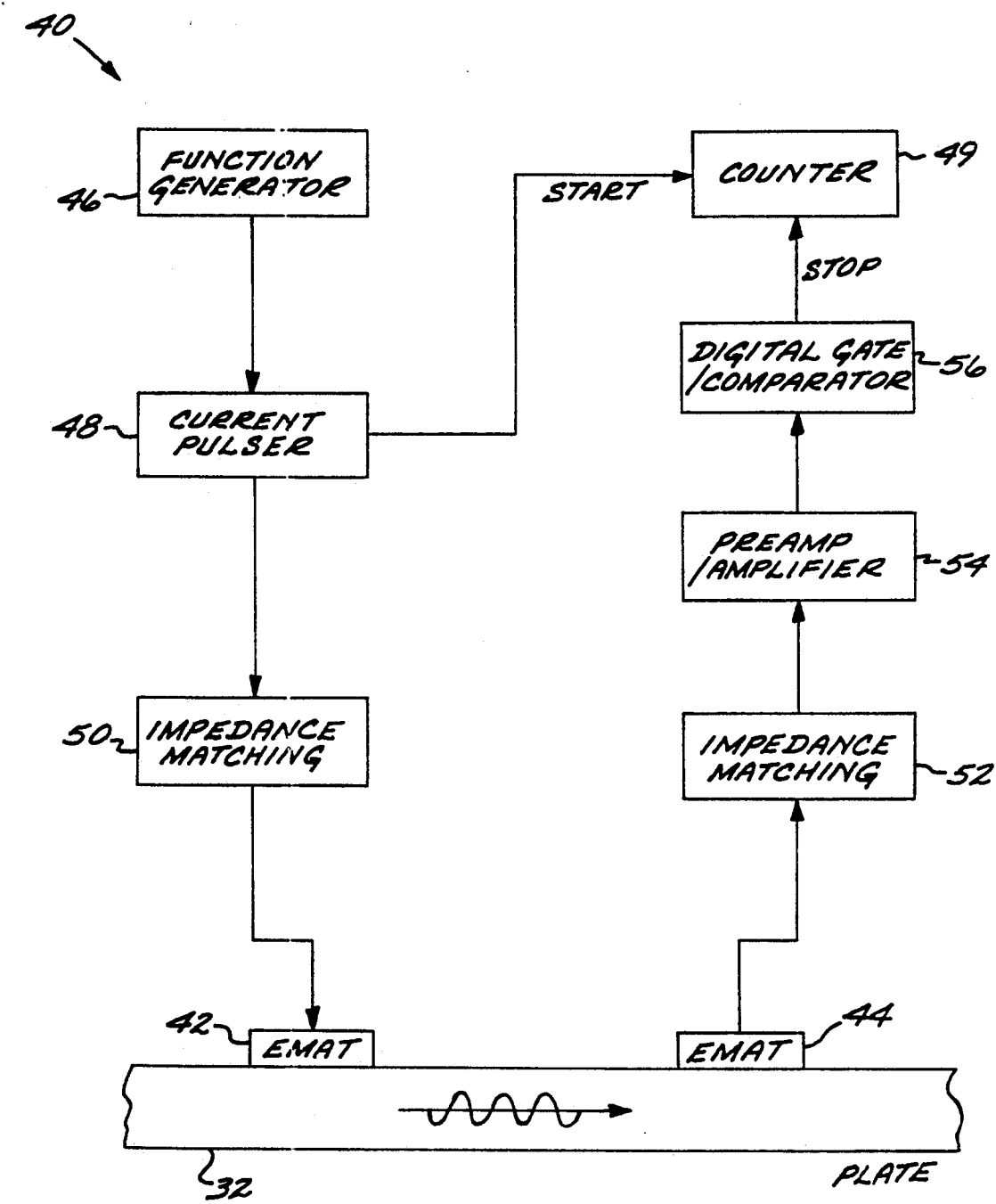
FIG. 3 is a diagrammatic illustration of the instrumentation of a paired EMAT system.

A system block diagram for an apparatus 40, for measuring ultrasonic velocities in sheets 32, utilizing a sending EMAT 42 and a receiving EMAT 44 is presented in FIG. 3. A function generator 46 generates a periodic signal, such as a square or sine wave, that is amplified by a current pulser 48 to a large current, typically 100 Amperes or more. The sending of the signal also provides a start command to a counter 49. The amplified signal is impedance matched by an impedance matcher 50 to the sending EMAT 42, which is of the type just discussed.

The ultrasonic Lamb wave signal produced by the EMAT 42 passes through the sheet 32 to the receiving EMAT 44. The signal received by the EMAT 44 is impedance matched to the amplifier circuit by an impedance matcher 52, and amplified by an amplifier 54. A digital gate/comparator 56 selects the proper portion of the waveform to use, which is a zero crossing in the preferred embodiment for reasons that will be explained. This selected value provides a stop command to the counter 49.

In one preferred embodiment using digital technology, the function generator 46 is a standard commercial chip generating a sine wave function, the current pulser 48 is a mosfet power amplifier, the impedance matcher 50 is a series tuning capacitor, the impedance matcher 52 is a shunt tuning capacitor and step up voltage transformer, the amplifier 54 is a low noise, high gain amplifier with a typical voltage noise of less than 2 nanovolts per square root Hertz, the digital gate/comparator 56 is a circuit that generates a pulse that stops the counter when the selected zero-crossing is sensed, and the counter 49 is a Fluke counter.

In a more preferred embodiment using analog technology, the function generator 46 is a Wavetek Model 190 function generator generating a sine wave function, the current pulser 48 is a Matec Model 5100 gating modulator with a model 515 A r.f. amplifier, the impedance matcher 50 is a series tuning capacitor, the impedance matcher 52 is a shunt tuning capacitor and step-up voltage transformer, the amplifier 54 is the receiver portion of a Panametrics 5055 P.R. pulser-receiver, the analog gate 56 is a Panametrics stepless gate model 5052 G that isolates the selected zero crossing in the received waveform, and the counter 49 is a Hewlett Packard 5335 A universal counter.

For improved precision, at least about 100 measurements are averaged to minimize the effect of any random electromagnetic interference in the operating environment. Typical precisions are 1 nanosecond or better, for typical arrival times of about 50 microseconds. The overall electronics precision is about 2 parts in 100,000.

FIG. 3 shows that the EMATs 42 and 44 are separated by a distance over which the ultrasonic wave propagates. The angular relationships of the EMATs 42 and 44 are shown relative to the sheet 32 in FIGS. 4 and 5, for two alternative mechanical constructions of the apparatus 40. In the preferred practice of the invention, the ultrasonic velocity in the sheet is measured in the plane of the sheet 32, but at three different angles to a rolling direction 60 of the sheet 32. The various measurements can be taken with at least one of the EMATs movable, FIG. 4, or with all EMAT's fixed.

Figure 4:
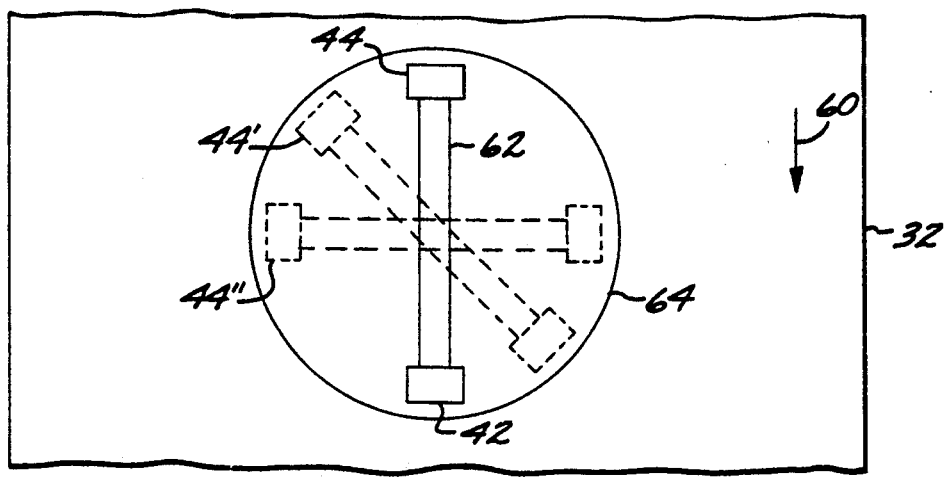
FIG. 4 is a schematic plan view of a measurement apparatus using two EMATs.

Referring to FIG. 4, the EMATs 42 and 44 are joined together by a rigid structure 62 mounted on a rotatable platform 64. The platform 64 can be rotated from a first position illustrated by the solid lines and the EMAT 44, to a second position illustrated in broken lines and the EMAT 44', to a third position illustrated in broken lines and the EMAT 44''. In the first position, the path traversed between the EMATs by the ultrasonic wave is parallel to the rolling direction 60, so that the determined ultrasonic velocity is termed $V_0$. In the second position, the path traversed between the EMATs by the ultrasonic wave is at an angle of 45 degrees to the rolling direction 60, so that the determined ultrasonic velocity is termed $V_{45}$. In the third position, the path traversed between the EMATs by the ultrasonic wave is at an angle of 90 degrees (or perpendicular) to the rolling direction 60, so that the determined ultrasonic velocity is termed $V_{90}$. In all cases the path lies in the plane of the sheet 32. (Other combinations of noncolinear velocities could be used, but the above convention is preferred to be consistent with the approach for defining the formability index.)

Figure 5:
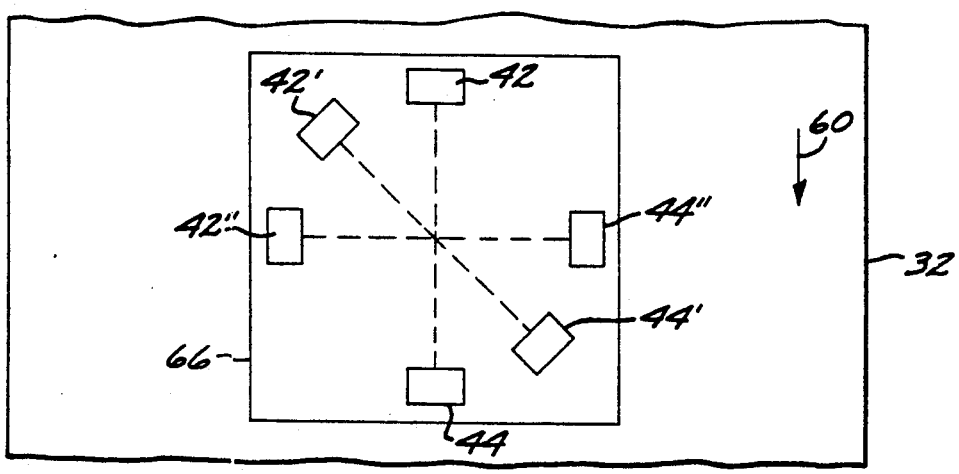
FIG. 5 is a schematic plan view of a measurement apparatus using six EMATs.

Another approach is illustrated in FIG. 5. A total of six stationary EMATs are used in pairs to obtain the same information as obtained by the apparatus of FIG. 4. The EMATs are supported on a base 66 that does not rotate with respect to the sheet 32. A set of receiving EMATs 44, 44', and 44" have a set of sending EMATs 42, 42', and 42" arranged such that the path length from EMAT 42 to EMAT 44 provides $V_0$, the path length from EMAT 42' to EMAT 44' provides $V_{45}$, and the path length from EMAT 42" to EMAT 44" provides $V_{90}$.

The arrangement of FIG. 4 has the advantages of electronic simplicity and reduced cost, and no need for multiplexing of electronics. Also, the ultrasonic velocity along any arbitrarily chosen path can be measured. The arrangement of FIG. 5 has the advantages of mechanical simplicity and that all three velocity measurements can be made exactly simultaneously, a desirable feature if the sheet 32 is moving relative to the base 66 as could be the case in an on line apparatus 40.

The velocity of an ultrasonic wave is calculated by measuring the distance travelled by the ultrasonic wave from the sending EMAT 42 to the receiving EMAT 44, and dividing by the time of flight. The time of flight is determined electronically by the counter 49 and associated electronics, and is quite accurate. However, as indicated previously, each EMAT has a finite length L parallel to the path length along which the velocity is measured. If one seeks to measure the distance travelled, there is inherently an ambiguity in knowing precisely the distance value unless care is taken to resolve the ambiguity. A calibration approach has been devised to avoid that ambiguity, and provide a correct and consistent value of distance.

In the first step of the calibration of the EMATs, the rigid structure 62 is replaced by a series of gage blocks that space the EMATs apart by controllable distances. The apparatus 40 is operated, and the arrival time measured as a function of the separating distance of the gage blocks, for a selected zero crossing of the wave form. That is, the ultrasonic wave has a number of crossing points, and one somewhere in the middle of the tone is selected for counting in all measurements. This technique is possible with the apparatus 40. The arrival time is graphed as a function of separating distance, and the slope of the graph is $1/V_{c,angle}$, where the "c" indicates a calibration value and "angle" indicates the angle with respect to the rolling direction. Normally, values of $V_{c,0}$, $V_{c,45}$, and $V_{c,90}$ would be determined. It is not necessary to know the actual distance travelled, due to the slope method of making the determinations.

The EMATs are then placed back into the rigid structure 62 (or the rigid base 66), with separations that are fixed but not known with the precision required. Arrival times are measured for each of the three orientations using the same zero crossing as used in the calibration, and the effective separating distance between the EMATs, $d_{eff}$, calculated in each case as the product of the measured arrival time and the appropriate value of $V_{c,angle}$. The distances $d_{eff}$ should be the same for all three orientations, but there is inevitably a small difference due to experimental error and a possible different mode of operation of the EMATs depending upon orientation. However, with the apparatus 40 as constructed the value of the difference in $d_{eff}$ for the different orientations divided by $d_{eff}$ is on the order of about 1/1000, thereby validating the technique and providing confidence that the value used is representative of the actual distance travelled by the ultrasonic wave as it propagates through the sheet 32 from EMAT 42 to EMAT 44. With this value of $d_{eff}$, measured velocities in tests of other samples are readily determined as $d_{eff}$ divided by measured arrival time.

Figure 6:
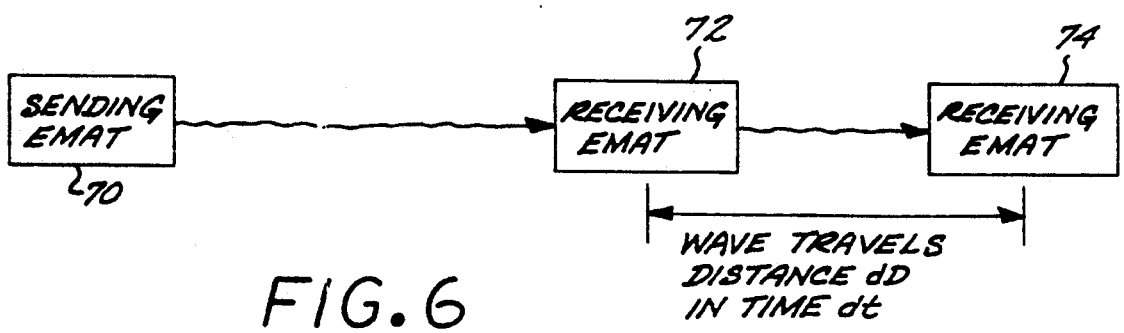
FIG. 6 is a schematic plan view of a three-probe technique using three EMATs for each measurement axis.

An alternative technique for obtaining precise velocities is illustrated in FIG. 6. In this approach, the three-probe technique, a single sending EMAT 70 propagates waves to two receiving EMATs 72 and 74, all three EMATs 70, 72, and 74 being colinear. (Equivalently, a three-probe array of two sending EMATs and a single receiving EMAT can be used.) The velocity is determined as the ratio dD/dt, where dt is the time differential between the receipt of a selected portion of a wave at the first receiving EMAT 72 and the second receiving EMAT 74 and dD is the distance between the longitudinal center of the receiving EMATs 72 and 74.

The measured velocities are the desired zero thickness limit of the phase velocity values only if the wavelength of the ultrasonic wave is much greater than the sheet or plate thickness under study, a condition satisfied in the preferred operating conditions of the invention. For an ultrasonic frequency of about 500 KHz (kilohertz), the wavelength is in the centimeter range. Where the thickness of the sheet being studied is on the order of one millimeter or less, the measured phase velocity is within about one percent of the limiting phase velocity. The limiting phase velocity is the measured phase velocity divided by a correction factor which is about 0.99 in the preferred embodiment of a one-millimeter thick sheet. The values of the correction factor for other relative values of the ultrasonic frequency and sheet thickness are determined from the information presented in R. B. Thompson et al., "A Comparison of Ultrasonic and X-ray Determinations of Texture in Thin Cu and Al Plates," Metallurgical Transactions, vol. 20A, pages 2431-2447 (1989), whose disclosure is incorporated by reference.

The procedure of the invention is implemented using the apparatus 40 and an approach like those just described for obtaining accurate velocity measurements. The preferred ultrasonic correlation parameter is preferably calculated as an effective velocity $V_b$, $$V_b = \tfrac{1}{4}(V_0 + V_{90} + 2V_{45}).$$

An alternative ultrasonic correlation parameter is dependent upon Young's modulus, $E_b$, as $$E_b = \tfrac{1}{4}PD(V_0^2 + V_{90}^2 + 2V_{45}^2)$$

where P is a Poisson factor of $(1-nu^2)$, nu being the Poisson's ratio, and D is the density of the steel. Either or both of these correlation parameters may be calculated from the results of measurements of sheets using the apparatus 40.

A formability index $r_b$ is calculated as $$r_b = \tfrac{1}{4}(r_0 + r_{90} + 2r_{45}).$$

This formability index is known in the industry and is conventionally determined by a destructive measurement. The value of r is the ratio of the transverse strain in the plane of the sheet to the transverse strain perpendicular to the plane of the sheet, for a tensile sample whose major deformation is in the indicated direction relative to the rolling direction. Engineers who study forming operations conventionally use $r_b$ to understand their results.

The present approach for determining $r_b$ ultrasonically yields results of direct utility to those who study the forming processes. The present approach also provides acceptability criteria evaluations. The formability engineers can often state from their studies that, to be successfully employed in a particular forming operation, a steel must have an $r_b$ value within certain limits. The present approach provides a quick, nondestructive measure of whether a steel will fall within those limits.

The present technique proceeds as follows. First, a calibration relationship between the ultrasonic correlation parameter and the formability index is prepared. For a number of samples of the material, such as steel sheet, which differ somewhat in composition, texture, heat treatment, rolling schedule, or other relevant parameter, the values of the ultrasonic correlation parameter $V_b$, or $E_b$, or otherwise as defined, are determined using the apparatus 40 and the procedure described previously. Tensile test samples are then prepared from the ultrasonically tested samples, and measured in the conventional manner to obtain the $r_b$ value for each sample. The measurement technique for the $r_b$ value, which is not a part of the present invention, is described in W. T. Lankford, S. C. Snyder, and T. A. Bauscher, Trans. ASM, vol. 42, pages 1197-1232 (1950) and ASTM Standard Technical Publication 390 (1965), published by the American Society for Testing and Materials, Philadelphia, Pa. A calibration relationship is then prepared from this information.

Figure 7:
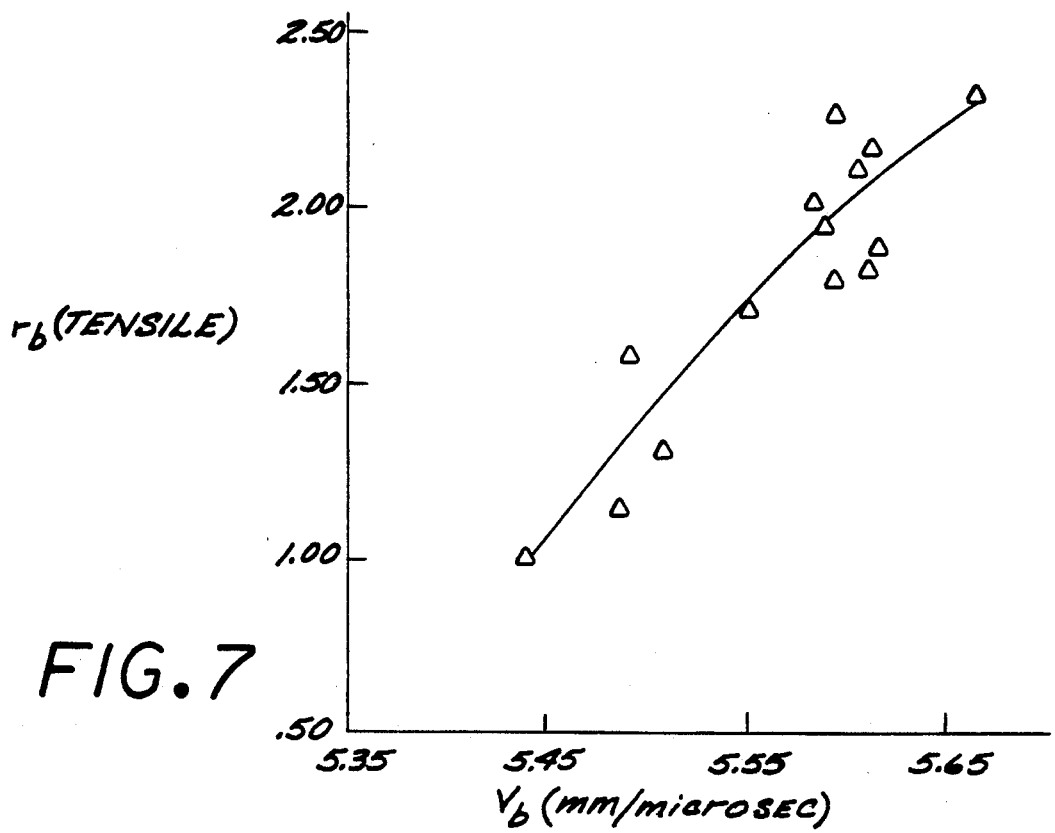
FIG. 7 is a graph of the formability index $r_b$ as a function of $v_b$.
Figure 8:
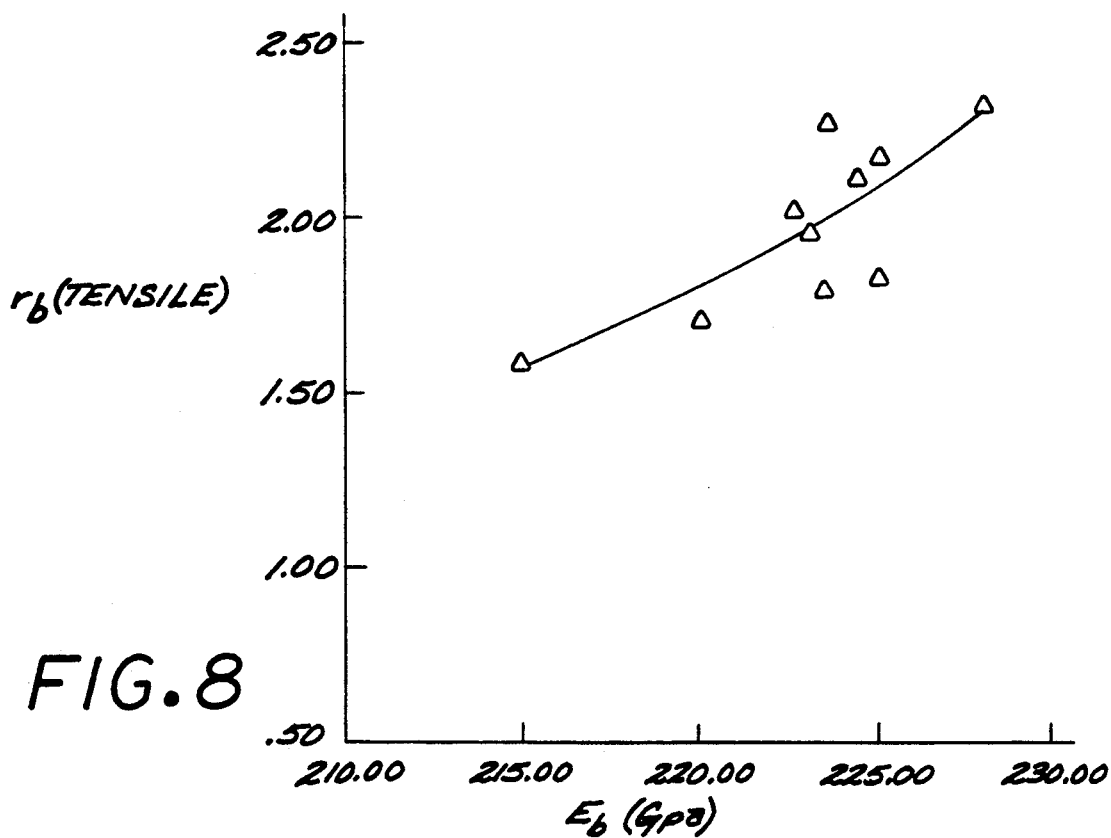
FIG. 8 is a graph of the formability index $r_b$ as a function of $E_b$.

FIG. 7 illustrates a calibration relationship for low carbon sheet steel between $r_b$ and $v_b$ for 15 samples. FIG. 8 illustrates a calibration relationship for low carbon sheet steel between $r_b$ and $E_b$ for the same 15 samples. Prior to the present invention, it had not been known whether such calibration relationships existed, not whether velocity measurements could be made in a noncontacting manner with sufficient precision to permit the definition of this type of calibration relationship.

There is observed some scatter from the lines drawn in each figure to represent the functional dependences. This scatter is expected due to the variation in the structure of the metal and the accumulation of possible experimental errors in this technique. However, a great virtue of the approach is that, as more data is accumulated, the statistical certainty of the calibration line is improved. Another important feature of the calibration technique is that the results of different studies, made by different persons and groups, can be integrated into a single data base in the form of the calibration curve of FIG. 6 or FIG. 7. This capability is conferred by the use of a velocity-based correlation rather than an arrival-time based correlation, which in turn is made possible by the apparatus calibration technique described previously.

Once a calibration between the ultrasonic correlation parameter and the formability index is prepared, then working samples can be evaluated. It will be recalled that the calibration specimens were destroyed in order to obtain actual values of the formability index $r_b$. For working specimens that are not to be destroyed, it is necessary only to measure the selected ultrasonic correlation parameter, preferably $v_b$ or $E_b$, and then use the calibration of FIG. 7 or 8, respectively, to obtain a value of $r_b$. This value of $r_b$ for a working sample is obtained without utilizing any couplant to couple the transducers to the specimen, without excising a sample from the sheet, and virtually instantaneously. The use of an ultrasonic measurement permits the entire thickness of the specimen to be sampled, not just the surface layers. The approach is therefore suitable for measurements wherein the sample and the measuring apparatus are stationary relative to each other, or where the sample is moving relative to the measuring apparatus.

The present invention thus provides a scientifically justified and industrially operable approach for evaluating the formability of sheet material. Although particular embodiments of the invention have been described in detail for purposes of illustration, various modifications may be made. Accordingly, the invention is not to be limited except as by the appended claims.

What is claimed is:

1. A process for nondestructively evaluating the formability of rolled metallic sheet, comprising the steps of:

measuring the ultrasonic velocities of sound in the plane of the sheet parallel to a rolling direction $V_0$, perpendicular to the rolling direction $V_{90}$, and at 45 degrees to the rolling direction $V_{45}$, each of said measurements being conducted without excising a sample from the sheet, and including the substeps of sending an ultrasonic wave through the sheet with a sending electromagnetic acoustic transducer, receiving the ultrasonic wave with a receiving electromagnetic acoustic transducer, the sending and receiving transducers having a fixed distance therebetween, measuring the time for a selected zero crossing of the ultrasonic wave to propagate from the sending transducer to the receiving transducer, and determining the ultrasonic velocity using an effective path length distance previously determined for the array of sending and receiving transducers;

calculating an ultrasonic correlation parameter dependent upon the measured ultrasonic velocities; and determining a formability index of the sheet from the calculated correlation parameter and a previously prepared calibration between the correlation parameter and the formability index.

* * * * *